US00PP36810P2

(12) United States Plant Patent
Smith

(10) Patent No.: US PP36,810 P2
(45) Date of Patent: Jul. 8, 2025

(54) ***PAEONIA* PLANT NAMED 'Smithopus7'**

(50) Latin Name: ***Paeonia* hybrid**
Varietal Denomination: Smithopus7

(71) Applicant: Donald R. Smith, Fairfield, CT (US)

(72) Inventor: Donald R. Smith, Fairfield, CT (US)

( * ) Notice: Subject to any disclaimer, the term of this patent is extended or adjusted under 35 U.S.C. 154(b) by 0 days.

(21) Appl. No.: 18/966,376

(22) Filed: Dec. 3, 2024

(51) Int. Cl.
*A01H 5/02* (2018.01)
*A01H 6/00* (2018.01)

(52) U.S. Cl.
USPC ..... Plt./316

(58) Field of Classification Search
USPC ..... Plt./226, 316
See application file for complete search history.

(56) References Cited

U.S. PATENT DOCUMENTS

PP33,910 P2 * 1/2022 Rat ..... A01H 6/00
Plt./316

* cited by examiner

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of intersectional hybrid (Itoh) *Paeonia* plant named 'Smithopus7' is disclosed, large red-purple flowers of semi-double to fully double form carried on strong stems, which present the flowers above and beyond the foliage. Plants have very attractive, dissected foliage, which lasts through the fall and is also highly disease resistant. Plants have a symmetrical, compact plant habit/shape which is excellent in the landscape. The new variety is a intersectional hybrid (Itoh) *Paeonia* normally produced as an outdoor ornamental garden plant.

2 Drawing Sheets

Figure 1:
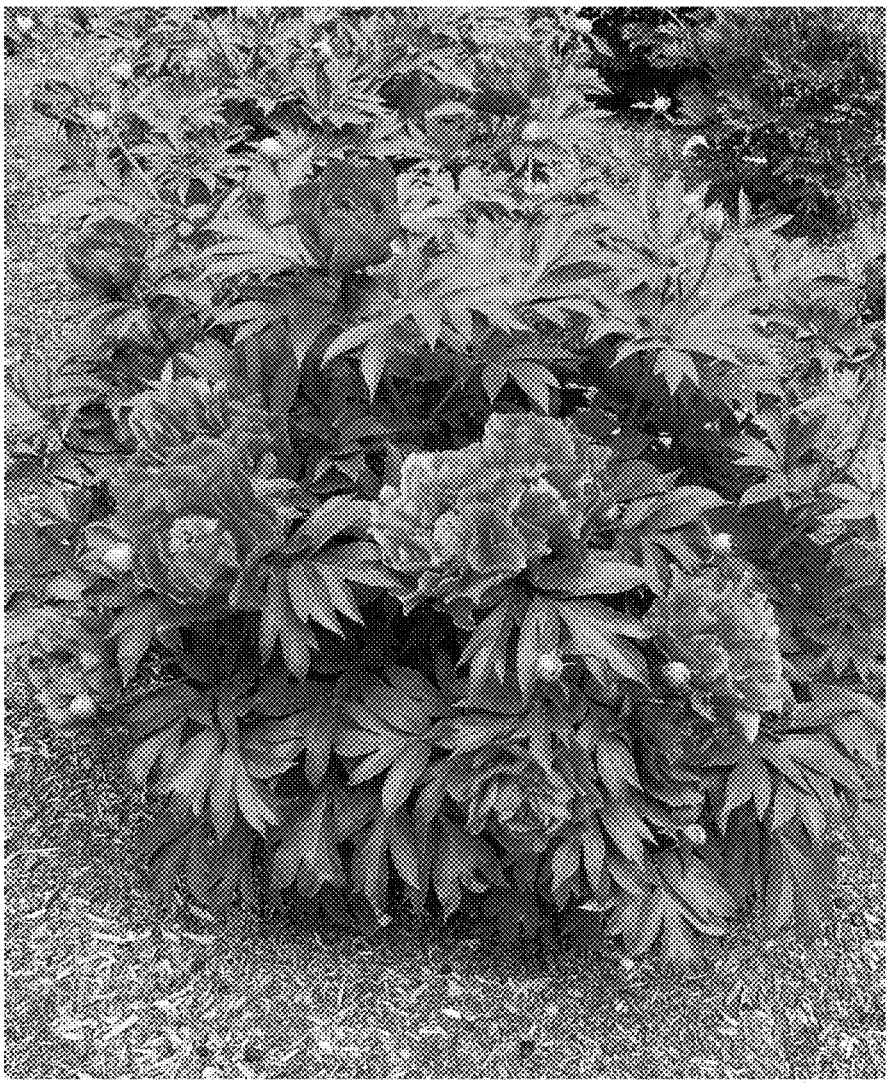

Latin name of the genus and species: *Paeonia* hybrid.
Variety denomination: 'Smithopus7'.

BACKGROUND OF THE INVENTION

The new cultivar is a product of a planned breeding program conducted by the inventor to produce new *Paeonia* hybrid cultivars with strong stems, large panicles, compact habits, and attractive flower aging. The crossing resulting in the new cultivar was made in summer of 2013 in a backyard in Windham, NH.

The seed parent is the cultivar *Paeonia* 'Martha W', unpatented. The pollen parent is *Paeonia* 'Nasa', unpatented. The new cultivar was found and selected by the inventor in 2017 in the same backyard in Windham, NH. Asexual reproduction of the new cultivar 'Smithopus7' was first performed at a research laboratory during 2018 in the Netherlands by tissue culture. Through subsequent confidential propagation, multiple additional generations have been reproduced, having shown that the unique features of this cultivar are stable and reproduced true to type.

Plants of the new cultivar were first sold Jul. 1, 2024 in the United States. This was from plant material originating from the inventor. Plants were advertised on a website from the Entity "Plants Nouveau", which has received a license, information and plant material directly from the inventor.

SUMMARY OF THE INVENTION

The cultivar 'Smithopus7' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Smithopus7.' These characteristics in combination distinguish 'Smithopus7' as a new and distinct *Paeonia* cultivar:

1. New variety is an intersectional hybrid (Itoh) peony from a cross of an herbaceous peony (lactiflora) with a hybrid tree peony.
2. It is a sterile first-generation hybrid with triploid (3n) ploidy level.
3. New variety has large red-purple flowers of semi-double to fully double form carried on strong stems, which present the flowers above and beyond the foliage
4. New variety has very attractive, dissected foliage, which lasts through the fall and is also highly disease resistant.
5. New variety has a symmetrical, compact plant habit/shape and makes an ideal landscape plant.

PARENT COMPARISONS

Plants of 'Smithopus7' are similar to plants of the seed parent in most horticultural characteristics, however, plants of 'Smithopus7' differ in the following:

1. Seed parent has fully herbaceous stems and growth habit, whereas the new variety has stronger semi-woody to woody stems and many above-ground buds, yet grows primarily as an herbaceous plant.
2. Seed parent has pink flowers of single form with 11-13 petals, whereas the new variety has semi-double to double flowers with many more petals (~36-38)
3. Seed parent blooms 1-2 weeks later than the new variety
4. Seed parent has many lateral flowers per stem, whereas the new variety has only 1 or 2.
5. Seed parent is highly fertile both ways, whereas the new variety is a sterile triploid Plants of 'Smithopus7' are similar to plants of the pollen parent in most horticultural characteristics, however, plants of 'Smithopus7' differ in the following:

1. Pollen parent is a woody tree peony hybrid that has winter hardy, woody stems, whereas the new variety has semi-woody stems that are much less winter hardy
2. Pollen parent has shrub-like plant and growth habit, whereas the new variety has mostly herbaceous habit
3. Pollen parent blooms 1-2 weeks before the new variety.

COMMERCIAL COMPARISON

Plants of 'Smithopus7' can be compared to plants of the commercial cultivar *Paeonia* intersectional hybrid 'Scarlet Heaven', unpatented. Plants of 'Smithopus7' are similar to plants of 'Scarlet Heaven' in most horticultural characteristics, however, plants of 'Smithopus7' differ in the following:

1. 'Scarlet Heaven' has dark red flowers of single flower form (10-12 petals), whereas the new variety has fully double flowers with 35-45 petals on average.
2. 'Scarlet Heaven' has poor foliage that becomes heavily spotted in early summer and dies back very early, whereas the new variety has completely unspotted, disease resistant foliage that lasts until late fall.
3. 'Scarlet Heaven' has average size flowers (5-6"), whereas the new variety has much larger flowers (7-8").

BRIEF DESCRIPTION OF THE PHOTOGRAPHS

The accompanying photograph in FIG. 1 illustrates in full color a typical plant of 'Smithopus7' grown in a field in Fairfield, CT. This plant is approximately 3 years old.

Figure 2:
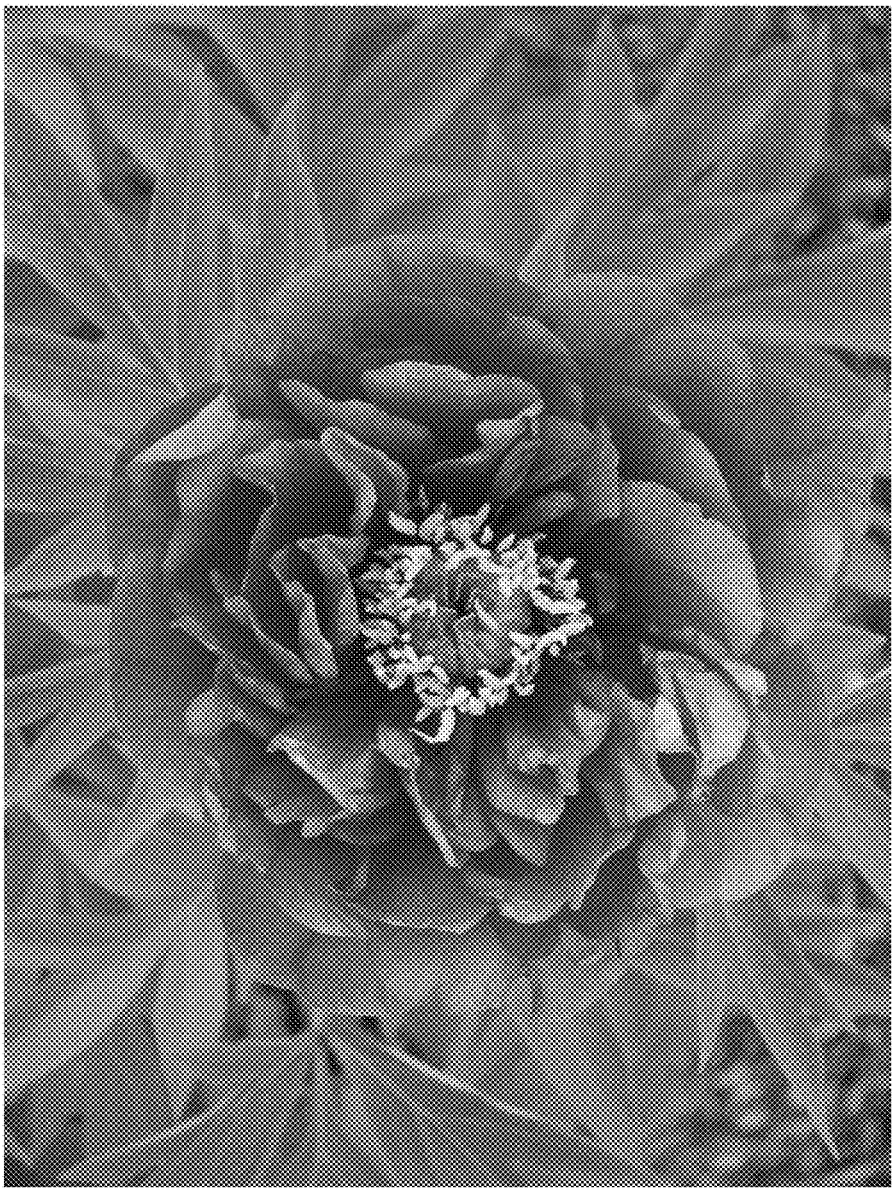

FIG. 2 illustrates in full color a close-up of a mature flower of 'Smithopus7'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'Smithopus7' plants grown outdoors in Camarillo, CA. The plants were 2 to 3 years old from large tubers, grown in 5-gallon pots. Temperatures ranged from 5° C. to 10° C. at night to 12° C. to 30° C. during the day. No artificial light, photoperiodic treatments were given to the plants. Measurements and numerical values represent averages of typical plant types.

Botanical classification: *Paeonia* hybrid 'Smithopus7'.

PROPAGATION

Typically by shoot tissue culture.

Root description: Freely branching storage root with numerous feeder roots. Roots various shades of tan and brown, not accurately measured with a color chart.

Tubers: Elongated, typically 5 to 12 cm long and 2 to 5 cm in diameter. Colored near Greyed-Orange 166A.

PLANT

Growth habit: Vigorous perennial herbaceous shrub. Semi-upright growth habit.

Height: Approximately 65 to 75 cm at opening of first flower.

Plant spread: Approximately 70 cm.

Stems:

Length: Approximately 40 to 50 cm.

Diameter: Average range 8 to 10 mm.

Strength: Strong.

Internode length: 6 to 12 cm, highly variable.

Color: Near RHS Yellow-Green 145A moderately covered in Greyed-Purple 185B.

Texture: Glabrous.

Age of plant described: Approximately 2 to 3 years.

FOLIAGE

Leaf: Alternate, pinnate compound, with an overall circular to ovate shape, which is slightly wider than long. Average fully expanded leaf 18 cm long and 22 cm wide, excluding the petiole. Horizontal to semi-erect attitude.

Primary leaflets:

*Shape*.—Obovate.

*Quantity and arrangement*.—3 primary leaflets further divided into 3 to 5 deeply divided secondary leaflets. All leaflets sessile.

*Length*.—Average range 9 to 12 cm.

*Width*.—Average range 8 to 12 cm.

Individual primary leaflet blades:

*Shape of blade*.—Broad ovate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very slightly reflexed downward.

Individual secondary leaflet blades:

*Shape of blade*.—Oblanceolate, variably incised.

*Apex*.—Acute.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very minutely reflexed downward.

*Color*.—Emerging Upper side: Near RHS Yellow-Green 145A, veins Greyed-Purple 185B. Under side: Near RHS Green 138B. Young Upper side: Near RHS Green 143B. Under side: Near RHS Green 138B. Mature Upper side: Near RHS Green 137D. Under side: Near RHS Green 138B.

*Venation*.—Type: Pinnate. Venation color upper side: Near RHS Yellow-Green 154B. Venation color under side: Near RHS Yellow-Green 144C.

*Petiole*.—Length: Average range 8 to 12 cm. Diameter: 5 to 6 mm. Color: Near RHS Yellow-Green 144C upper surface flushed Greyed-Purple 185B. Texture: Glabrous.

FLOWER

Natural flowering season: Flowering begins early May in Southern California. Flowering extends throughout the Summer, depending on environmental conditions.

Inflorescence type and habit: Double form with conspicuous stamens. 3 to 4 loose whorls. Shape regularly round. Erect flower attitude.

Flower longevity on plant: Approximately 10 days on the plant. Varies considerably with environmental conditions.

Quantity of flowers: 1 to 2 per stem. 8 to 12 flowering stems per plant.

Flower size:

*Diameter*.—Approximately 17 to 20 cm.

*Depth*.—Approximately 5 to 7 cm. (Flower height).

Peduncle:

*Length*.—Average length 6 to 12 cm.

*Diameter*.—Approximately 5 mm.

*Color*.—Near RHS Yellow-Green 145A streaked Greyed-Purple 185B.

*Strength*.—Strong.

*Texture*.—Glabrous and ribbed.

Petals:

*Petal arrangement*.—3 to 4 loose whorls of about 10 to 15 petals each.

*Size*.—Length: Average 6 cm. Width: Average 4 cm.

*Shape*.—Obovate.

*Margin*.—Entire. Lightly ruffled.

*Apex*.—Emarginate.

*Base*.—Broad attenuate.

*Texture*.—Smooth, glabrous all surfaces.

*Aspect*.—Strongly recurved up.

Color: Petals: When opening: Opening: Upper surface: Near RHS Red-Purple 60A. Lower surface: Near RHS Red-Purple 60D flushed 59D. Fully opened: Upper surface: Near RHS Red-Purple 71C. Lower surface: Near RHS Red-Purple 71D flushed 72D.

Petaloids: Not present.

Bud:

*Shape*.—Globular.

*Length*.—Approximately 2 cm.

*Diameter*.—Approximately 2 cm.

*Color*.—Near RHS Red-Purple 60A.

*Sepals*.—Quantity: 4. Length: 1.8 cm. Width: 2 cm. Shape: Obovate. Aspect: Cupped. Attitude: Horizontal. Apex: Rounded. Base: Truncate. Margin: Entire. Color Interior Surface: RHS Green 143C, lightly flushed Red-Purple 59C. Exterior Surface: RHS Green 143C, heavily flushed Red-Purple 59C. Texture: Glabrous.

*Fragrance*.—Faint musky scent.

REPRODUCTIVE ORGANS

Androecium:

*Stamens*.—Quantity: 100 to 120. Length: 1.5 to 2.4 cm. Filament Color: Red-Purple 60D.

*Anthers*.—Shape: Linear. Length: 1 mm. Color: Yellow 12A. Gynoecium:

*Pistil*.—Type: Compound. Petaloid, stigma only. Number: 4. Carpel Length: 1.7 cm. Carpel Width: 8 mm. Openness of disc: Partly open. Stigma: Petaloid. 3 mm long and 4 mm in diameter. Very hard. Shape: Irregular kidney. Color: Near RHS Red-Purple 71A. Ovary color: Near RHS Yellow-Green 145C flushed Red-Purple72C.

OTHER CHARACTERISTICS

Disease and pest resistance: Observed resistance to foliar diseases of *Paeonia*. No additional resistance nor susceptibility to the normal diseases and pests of *Paeonia* has been observed.

Temperature tolerance: Typically USDA Zones 3 to 8.

Fruit/seed production: Not observed.

What is claimed is:

1. A new and distinct cultivar of *Paeonia* plant named 'Smithopus7' as herein illustrated and described.

* * * * *